US012533488B2

(12) United States Patent
Leeflang et al.

(10) Patent No.: US 12,533,488 B2
(45) **Date of Patent: *Jan. 27, 2026**

(54) ISOLATION AND ATTACHMENT CATHETERS AND METHODS FOR USING THEM

(71) Applicant: CLPH, LLC, Palo Alto, CA (US)

(72) Inventors: Stephen A. Leeflang, Sandy, UT (US); Christian S. Eversull, Palo Alto, CA (US)

(73) Assignee: CLPH, LLC, West Valley City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/688,523

(22) Filed: Mar. 7, 2022

(65) Prior Publication Data

US 2022/0296853 A1 Sep. 22, 2022

Related U.S. Application Data

(63) Continuation of application No. 15/729,661, filed on Oct. 10, 2017, now Pat. No. 11,266,810.

(Continued)

(51) Int. Cl.

| | |
|---|---|
| ***A61M 25/00*** | (2006.01) |
| ***A61B 17/00*** | (2006.01) |
| ***A61B 17/30*** | (2006.01) |
| ***A61B 17/34*** | (2006.01) |
| ***A61M 25/01*** | (2006.01) |

(52) U.S. Cl.

CPC .... *A61M 25/0084* (2013.01); *A61M 25/0045* (2013.01); *A61M 25/005* (2013.01); *A61M 25/0108* (2013.01); *A61M 2025/0046* (2013.01); *A61M 2025/0089* (2013.01);

(Continued)

(58) Field of Classification Search

CPC .......... A61M 25/0084; A61M 25/0045; A61M 25/005; A61M 25/0108; A61M 25/0147; A61M 2025/0046; A61M 2025/0089; A61M 2209/088; A61M 2210/125; A61M 25/04; A61M 25/0082; A61B 2017/00247; A61B 2017/308; A61B 17/3478

See application file for complete search history.

(56) References Cited

U.S. PATENT DOCUMENTS

| | | | | |
|---|---|---|---|---|
| 11,266,810 | B2 * | 3/2022 | Leeflang | A61M 25/005 |
| 2008/0009747 | A1 * | 1/2008 | Saadat | A61B 1/04<br>604/510 |

(Continued)

*Primary Examiner* — Alireza Nia
*Assistant Examiner* — Hamza A Darb
(74) *Attorney, Agent, or Firm* — William A. English; Vista IP Law Group LLP

(57) ABSTRACT

Systems and methods are provided for navigating within the heart and attaching to the wall of the heart for performing injection of one or more agents into tissue. The system includes an outer catheter, a mid catheter slidably disposed within a lumen of the outer catheter, and a needle catheter slidably disposed within a lumen of the mid catheter. The mid catheter includes a vacuum hood attached to a mid catheter distal end such that a radiopaque distal tip of the mid catheter extends into the vacuum hood. The vacuum hood includes at least two radiopaque features, the spatial relationship of which visibly changes under fluoroscopy when the vacuum hood is under sealed vacuum.

23 Claims, 7 Drawing Sheets

Related U.S. Application Data

(60) Provisional application No. 62/406,086, filed on Oct. 10, 2016.

(52) U.S. Cl.
CPC ... *A61M 25/0147* (2013.01); *A61M 2209/088* (2013.01); *A61M 2210/125* (2013.01)

(56) References Cited

U.S. PATENT DOCUMENTS

| | | | | |
|---|---|---|---|---|
| 2015/0258270 | A1 * | 9/2015 | Kunis | A61M 5/00 604/506 |
| 2018/0125532 | A1 * | 5/2018 | Kassab | A61K 9/0019 |

* cited by examiner

ISOLATION AND ATTACHMENT CATHETERS AND METHODS FOR USING THEM

RELATED APPLICATION DATA

The present application is a continuation of co-pending application Ser. No. 15/729,661, filed Oct. 10, 2017, issuing as U.S. Pat. No. 11,266,810, which claims benefit of U.S. provisional Ser. No. 62/406,086, filed Oct. 10, 2016, the entire disclosures of which are expressly incorporated by reference herein.

FIELD OF THE INVENTION

The present invention relates generally to apparatus, systems, and methods for performing medical procedures, and, more particularly, to catheters adapted to attach to and/or isolate a portion of the heart wall during a procedure, e.g., during injection of one or more agents into the myocardium.

BACKGROUND

Minimally invasive devices are frequently used to perform procedures within body lumens and chambers, including the heart. Such procedures include making injections of cells, agents, filler materials, and/or other substances into the myocardium by minimally invasive, e.g., catheter-based, approaches. During such procedures, it is important to identify the correct anatomical position for each injection, navigate to that position, and maintain the selected position while a needle or other injection device is introduced into the tissue, the injection is performed, and the injection device is subsequently removed. For example, heart motion may make precise needle positioning difficult. Further, unexpected or excessive movement of an exposed needle may cause trauma, such as laceration or perforation. Further, inadvertent or premature movement of the needle out of tissue may risk loss of injected material and/or embolic complications.

Thus, devices and methods that enhance stability of a catheter or other device and/or isolate the location of treatment during such procedures would be beneficial.

SUMMARY

The present invention is directed to apparatus, systems, and methods for performing minimally invasive medical procedures, e.g., within a patient's heart. More particularly, the present invention is directed to catheters including an attachment, stabilization, and/or isolation element that employs a vacuum source and which may be used during injection of agents, cells and/or other material into tissue including the myocardium or other tissue of the heart.

Catheters for performing injections may include an attachment, stabilization and or isolation element, e.g., employing suction/vacuum to attach to the wall of the heart. For example, an expandable tip, hood, cup or other element may be disposed at the distal end of the catheter to enable attachment or increased stability relative to the heart wall during a procedure. In the case of making injections into the wall of the heart, a number of unique challenges and risks arise, which may be addressed by one or more of the apparatus, systems, and methods described herein.

In one embodiment, a catheter may include a vacuum hood including one or more radiopaque features adapted to clearly identify the heart wall, elucidate needle penetration into tissue, and/or demonstrate secure attachment of the vacuum hood to tissue. In another embodiment, a catheter may include a vacuum hood adapted to enable needle penetration into tissue while preventing perforation of the heart wall. In yet another embodiment, a catheter may include a vacuum hood adapted to generally reduce trauma to the vasculature, heart chamber, valves, and/or other tissue structures.

In accordance with another embodiment, a telescoping catheter system may be provided that is adapted to enable clear identification of attachment to the heart wall.

In a further embodiment, a catheter may include a vacuum hood adapted to enable oblique needle entry and securement into the heart wall.

In another embodiment, a catheter may include a vacuum hood adapted to capture stray material before, during, or after injection into tissue.

In yet another embodiment, a catheter system may be provided that includes a vacuum hood, vacuum lumen, and vacuum source adapted to minimize clotting and embolic potential of aspirated blood.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE EXEMPLARY EMBODIMENTS

Figure 1:
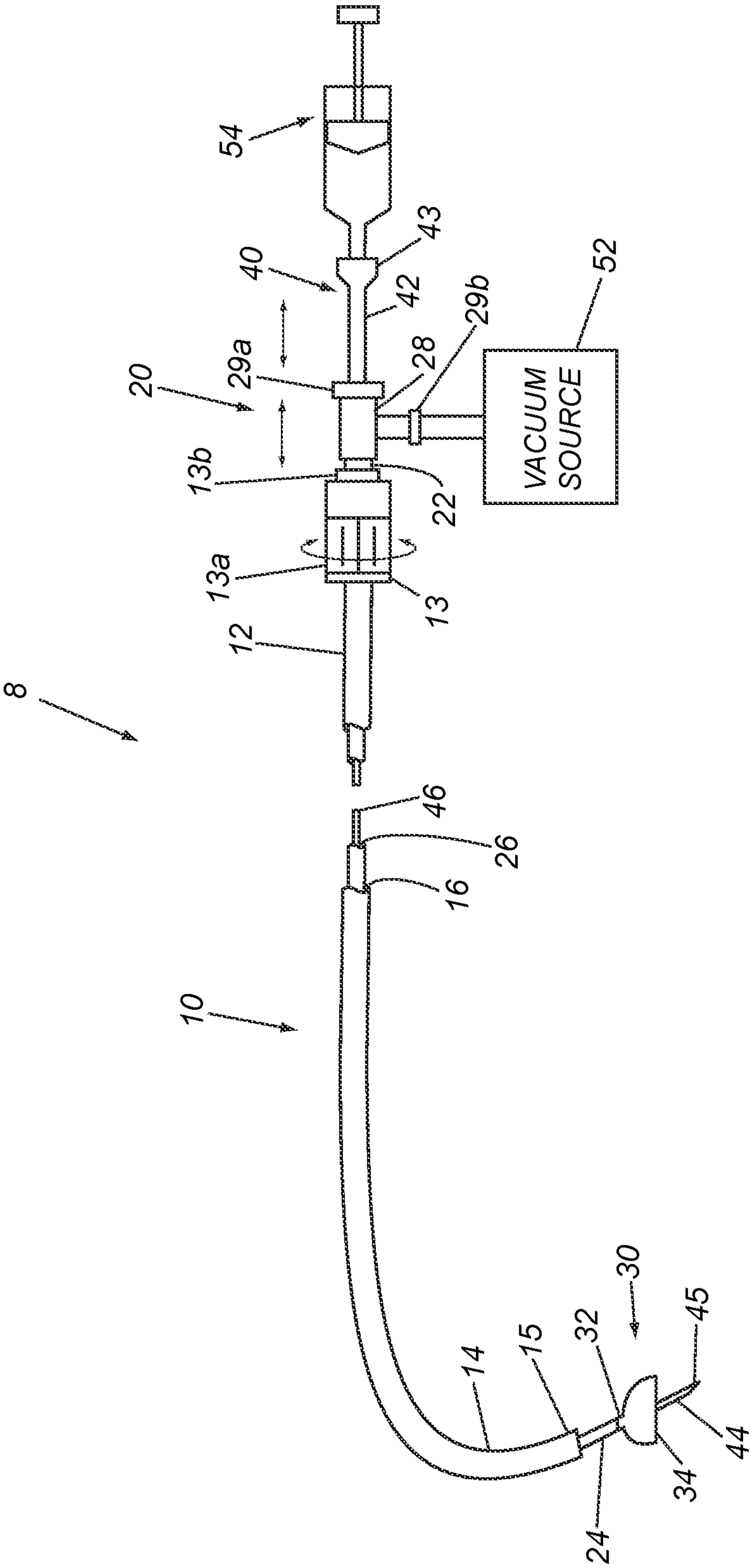
FIG. 1 is a side view of an exemplary embodiment of a catheter system including an outer catheter, a mid catheter with distally attached vacuum hood, and an inner injection catheter all slidable relative to one another, the system also including a vacuum source communicating with the lumen of the mid catheter and a source of one or more agents.

Turning to the drawings, FIG. 1 shows an exemplary embodiment of a catheter delivery system 8 including a first or outer catheter or sheath 10, a second or mid catheter 20 carrying a vacuum hood 30, and a third or injection catheter or needle device 40, which may be used to perform a procedure within a patient's body, e.g., perform one or more injections into tissue, such as within the myocardium of a patient's heart (not shown). In addition to the catheters 10, 20, 30, the system 8 may include one or more additional components, e.g., a vacuum source 52, such as a syringe or vacuum pump, and a source of one or more agents 54, e.g., including one or therapeutic and/or diagnostic materials, such as cells, filler materials, gels, and the like. Optionally, the system 8 may include one or more additional devices, e.g., a source of fluid, and/or one or more guidewires, sheaths, and the like (not shown) for facilitating introduction of the catheters into a patient's body.

The outer catheter 10 generally includes a proximal end 12 including a hub or handle 13, a distal end 14 sized for introduction into a patient's body and terminating in a distal tip 15, and one or more lumens, e.g., lumen 16, extending between the proximal and distal ends 12, 14, thereby defining a longitudinal axis 18 for the catheter 10 and system 8. Optionally, a distal portion of the outer catheter 10 may be pre-shaped, deflectable, and/or otherwise directable to manipulate the distal end 14, e.g., to facilitate navigation within a patient's vasculature and/or chambers of the heart. For example, the outer catheter 10 may include one or more pull wires or other steering elements (not shown) coupled between the distal tip 15 and an actuator 13*a* on the handle 13, e.g., for directing the distal end 14 between a substantially straight and one or more curvilinear shapes, e.g., the shape shown in FIG. 5.

The outer catheter 10 may be constructed using known materials and methods, e.g., including a liner surrounding the lumen 16, an intermediate reinforcing layer (e.g., a braid, coil, and the like), and one or more outer jackets (all not shown for simplicity). In an exemplary embodiment, the liner may include one or more coatings, e.g., a hydrophobic, hydrophilic, or other lubricious coating, and/or may be formed from lubricious material to facilitate introduction and/or movement of the mid catheter 20 or other instrument within the lumen 16. Optionally, the outer catheter 10 may include one or more radiopaque markers, e.g., rings, bands, and the like, at desired locations along its length, e.g., at the distal tip 15 and/or spaced apart from one another adjacent the distal tip 15 (not shown).

In addition, the outer catheter 10 may include one or more additional components on the handle 13, e.g., a port 13*b* communicating with the lumen 16 and including one or more valves, e.g., a hemostatic valve (not shown) to provide a fluid-tight seal yet accommodate inserting the mid catheter 20 and/or other devices into the lumen 16. Optionally, the handle 13 may also include a side port including a Luer connector or other fitting (not shown) for coupling a source of fluid to the handle 13 and delivering the fluid into the lumen 16 (or an additional lumen, not shown) of the catheter 10. Exemplary embodiments of catheters that may be used as the outer catheter 10 are disclosed in U.S. Publication No. 2016/0082226, the entire disclosure of which is expressly incorporated by reference herein.

With continued reference to FIG. 1, the mid catheter 20, similar to the outer catheter 10, generally includes a proximal end 22, a distal end 24, and one or more lumens, e.g., lumen 26, extending between the proximal and distal ends 22, 24. In addition, the mid catheter 20 includes an expandable vacuum hood 30 carried on the distal end 24 adjacent a distal tip 25 thereof, as described further elsewhere herein. The mid catheter 20 may be sized to be at least partially received within the outer catheter 10, e.g., having a diameter between about six and ten French (2.0-3.3 mm), or between about six and eight French (2.0-2.7 mm), such that the distal end 24 may be inserted through the port 13*b* in the handle 13 into the lumen 16 of the outer catheter 10, at any time during use, e.g., to deploy the vacuum hood 30, as described further elsewhere herein. Alternatively, the mid catheter 20 may be pre-loaded within and/or unremovable from the outer catheter 10, e.g., with the distal end 24 and vacuum hood 30 initially positioned within the lumen 16, e.g., proximal to the distal end 14 of the outer catheter 10. In another alternative, the hood 30 may be initially provided extending from the distal end 14 of the outer catheter 10, e.g., abutted against the distal tip 15, which may provide an atraumatic bumper during advancement of the outer catheter 10, e.g., through a valve or other tissue structure (not shown). In either case, the mid catheter 20 is configured to slide axially and/or rotationally relative to the outer catheter 10, e.g., to provide an additional degree of freedom when navigating within the vasculature or heart and/or to deploy and withdraw the vacuum hood 30 when desired from the outer catheter distal end 14, also as described elsewhere herein.

The mid catheter 20 may be constructed using similar materials and methods as the outer catheter 10, e.g., including a lubricious liner and/or coating, an intermediate reinforcement layer, and one or more outer jackets (not shown). Furthermore, the mid catheter 20 may include a relatively flexible distal segment, e.g., offset a predetermined distance proximal to the distal tip 25 and vacuum hood 30, to facilitate tracking and/or atraumatic navigation. For example, the flexible segment may be sufficiently flexible to stabilize the mid catheter 20, dampen movement, and/or prevent hood detachment, e.g., when the hood 30 is attached to a moving structure such as a wall of a beating heart (not shown), as described elsewhere herein.

The mid catheter 20 also includes a handle or hub 28 on the proximal end 24 including one or more ports, e.g., port 29*a* including one or more valves, e.g., a hemostatic valve (not shown) to provide a fluid-tight seal yet accommodate inserting the injection catheter 40 into the lumen 26. In addition, the handle 28 may also include a first side port 29*b* communicating with the lumen 26 of the mid catheter 20, which may include a Luer fitting or other connector (not shown) for coupling a vacuum source 52 to the side port 29*b*. Optionally, the handle 28 may include one or more additional side ports (not shown), e.g., a second side port communicating with a secondary lumen within the mid catheter 20 to which a source of fluid, e.g., a syringe (also not shown) may be coupled for delivering heparin, heparinized saline and/or other anticoagulant or dilutive media into the secondary lumen, as described elsewhere herein. Alternatively, or in addition, the mid catheter proximal end 24 may be fitted with a valve or hub including a valve, e.g., to seal on the body of a needle passing through the lumen 26 of the mid catheter 20, e.g., the body of the injection catheter 40 (not shown). A hole or passage (also not shown) may be provided in the side wall of the mid catheter 20, e.g., communicating with a lumen, e.g., the primary lumen 26 of the mid catheter 20, e.g., through which fluid may be infused or aspirated, e.g., to transmit negative pressure or vacuum to the vacuum hood 30.

Figure 2:
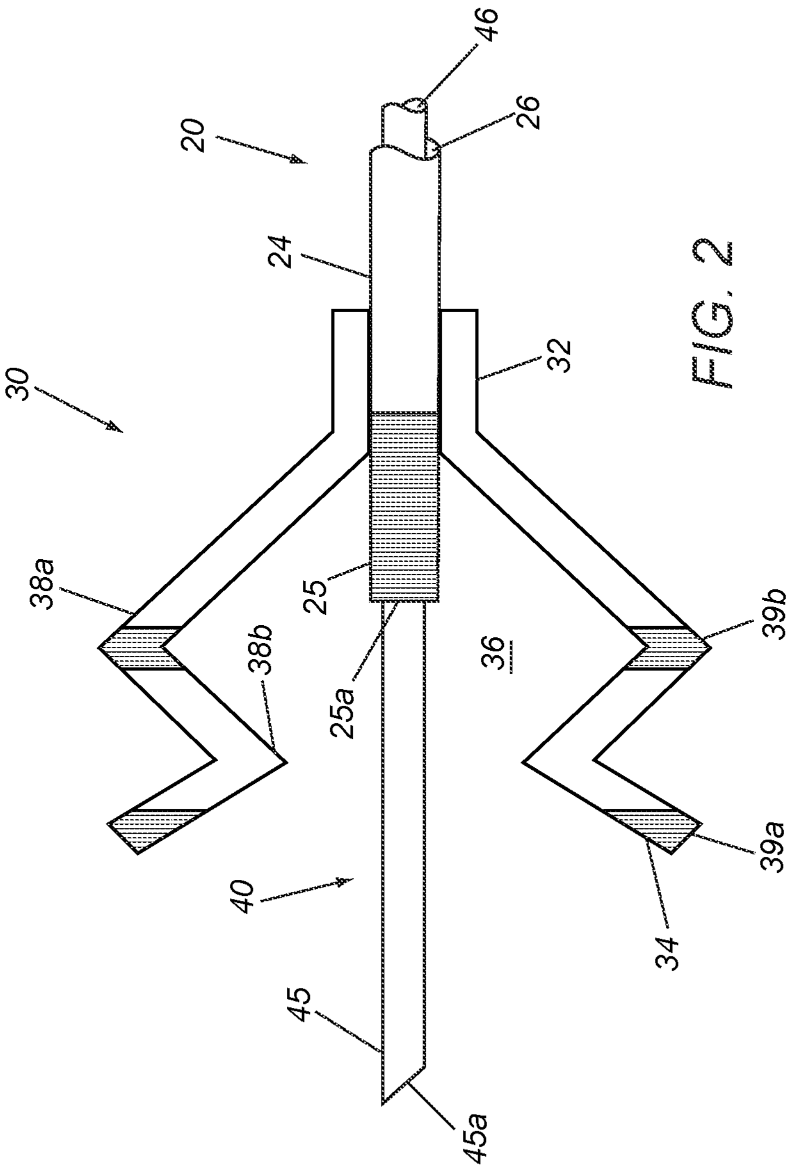
FIG. 2 is a cross-sectional side view of an exemplary embodiment of a vacuum hood with radiopaque features that may be provided on the hood and associated catheter, such as the mid catheter of FIG. 1.

With additional reference to FIG. 2, a vacuum hood 30 is provided on the distal end 24 of the mid catheter 20 that includes an expandable element, e.g., a hood, cup, suction cup, sucker, and the like, which may be expandable between a collapsed configuration and an expanded configuration, e.g., having a diameter or other cross-sectional dimension larger than the outer diameter of the mid catheter 20 in the expanded configuration. In the embodiment shown in FIG. 2, the vacuum hood 30 includes a first or proximal end 32 that may be attached to the mid catheter 20 and a distal end or face 34 sized and/or shaped to be placed against a tissue surface (not shown), as described elsewhere herein. The vacuum hood 30 at least partially encloses an interior region or chamber 36 that is in communication with the primary lumen 26 of the mid catheter 20 and the distal face 34, e.g., such that vacuum may be generated within the chamber 36, and consequently at the distal face 34, via the primary lumen 26 from the vacuum source 52 coupled to the side port 29*b*. For example, the vacuum hood 30 may have a generally conical or frustoconical shape, a hemi-spherical, or other bulbous shape, e.g., that increases in size from the proximal end 32 to the distal face 34, e.g., generally symmetrical to the longitudinal axis 18.

In the collapsed configuration, the vacuum hood 30 may be rolled, folded, or otherwise compressed to a size sufficient to pass through the primary lumen 26, yet may be resiliently biased to assume the expanded configuration when deployed from the lumen 26. Optionally, the hood 30 may include one or more supports or features (not shown) formed into or attached to the hood material to bias the hood towards the expanded configuration and/or to bias the distal face 34 to open to a desired size and/or shape. For example, the folds or other features and/or markers may also provide support to the hood 30, e.g., to prevent the hood 30 from collapsing radially inwardly.

The vacuum hood 30 may be constructed of a generally flexible or compliant material, such as silicone, urethane, or polyether block amide, such that the vacuum hood 30 may be passed through and/or contact tissue structures, e.g., within a patient's vasculature and/or heart, without causing trauma, but having sufficient stiffness such that, when a vacuum is applied, the vacuum hood 30 does not entirely collapse. In particular, the vacuum hood 30 may be constructed with features to enable at least the distal face 34 to maintain a generally open shape with relatively consistent cross-sectional area, e.g., as described further elsewhere herein. It will be appreciated that the force with which the vacuum hood 20 is able to attach to tissue, e.g., to a wall of a heart, may be a function of both the vacuum applied and the cross-sectional area of the distal face 34 interfacing with the tissue. Thus, the force of attachment may be modulated by modulating these two parameters.

FIG. 2 shows a side view of an exemplary embodiment of the vacuum hood 30 attached to the distal end 24 of the mid catheter 20. In the embodiment shown, the proximal end 32 of the vacuum hood 30 may be attached to the distal end 24 proximal to a distal tip 25 of the mid catheter 20, i.e., such that the mid catheter distal tip 25 extends a predetermined distance into the chamber 36 of the vacuum hood 30. The vacuum hood 30 may be substantially permanently attached to the mid catheter distal end 24, e.g., by one or more of bonding with adhesive, interference fit, sonic welding, fusing, and the like.

Optionally, the vacuum hood 30 may include one or more annular gussets, folds, thin areas, thick areas, or other features 38 that support the hood 30 yet allow axial movement of the distal face 34 towards and/or away from the proximal end 32, e.g., to enable foreshortening of the hood 30 when vacuum is present within the chamber 36 of the hood 30, e.g., when attached to a wall of a heart or other tissue structure, as described further elsewhere herein. For example, the features 38 may simply be a thinning in the wall of the hood 30, more compliant material, a pleat, fold, bellows, or other mechanical feature, e.g., extending circumferentially around one or more locations along the length of the hood 30.

For example, in the embodiment shown in FIG. 2, the hood 30 may include an annular outward fold 38*a* and an annular inward fold 38*b*, thereby defining a bellows that allows the hood 30 to expand and contract axially, which may facilitate placement against a tissue structure, e.g., a wall of heart that is not oriented perpendicular to the longitudinal axis 18, as described further elsewhere herein. For example, the folds 38 may symmetrically compress or elongate, or may accommodate one side of the hood 30 elongating while an opposite side is compressed. Alternatively, multiple annular outward and/or inward folds may be provided, if desired, e.g., to increase the axial compression and/or elongation distance that the distal face 34 may be deflected relative to the mid catheter distal end 24.

In addition or alternatively, the hood 30 may include a flexible proximal region (not shown), e.g., spaced a predetermined distance from the proximal end 32, which may allow the distal face 34 of the hood 30 to pivot or gimbal relative to the longitudinal axis 18 and the proximal end 32 Such annular folds 38, features, and/or flexible regions may be molded or otherwise formed directly into the hood material or may be constructed by forming the hood 30 from multiple segments, e.g., annular segments, formed from different materials that are attached together.

The mid catheter distal tip 25 may include one or more outlet ports communicating with the primary lumen 26 of the mid catheter 20. For example, as shown in FIG. 2, the distal tip 25 includes an axial outlet 25*a* through which a needle tip 45 may extend during an injection. Optionally, the distal tip 25 may include one or more side ports (not shown) proximal to the outlet 45*a*, e.g., to facilitate a vacuum being applied to the chamber 36 when the needle tip 45 is positioned through the outlet 25*a*.

In addition, the mid catheter 20 and/or vacuum hood 30 may include one or more radiopaque markers to facilitate locating and/or positioning the distal end 24 and/or vacuum hood 30 using fluoroscopy or other imaging during a procedure, e.g., during introduction into and/or manipulation within a body lumen, placement of the hood distal face 34 against a tissue structure, and/or deployment of the injection catheter 40. For example, as shown in FIG. 2, the entire mid catheter distal tip 25 may be made from radiopaque material or may include one or more radiopaque rings, bands, or other discrete markers. Various methods may be used to make the distal tip 25 radiopaque, including doping of the outer jacket of the distal end 24 material within the chamber 36 with barium, bismuth, tungsten or other radiodense materials as known in the art. Alternatively, a separate annular tip may be formed from radiopaque material and attached to the mid catheter distal end 24. In another alternative, radiopaque bands or elements made of platinum, platinum/iridium, gold, tungsten or other radiodense metals may be provided on the distal tip 25, which may simply be an extension of the distal end 24, as is also known. Optionally, one or more radiopaque markers may be provided on the distal end 24 of the mid catheter body 20 proximal to the distal tip 25, if desired, e.g., using similar methods.

The extension of the mid catheter distal tip 25 into the chamber 36 of the vacuum hood 30 may provide structural support, preventing collapse of the hood 30 under vacuum, and/or may provide a fluoroscopically visible marker in known relation to the position of the vacuum hood 30 for navigation. For example, when vacuum is applied to the vacuum hood 30, a proximal segment adjacent the proximal end 32 may have a tendency to collapse; in fact, the hood 30 may be designed specifically such that the proximal segment collapses, e.g., in order for the entire hood 30 to be more easily sheathed, pulled into a mid catheter lumen 26, and/or otherwise constrained, e.g., for introduction into the body. If the proximal segment were to collapse fully under vacuum, fluid communication to the distal face 34 of the hood 30 may be interrupted and no attachment to tissue achieved. Extending the distal tip 25 of the mid catheter 20 at least partially through the chamber 36 of the hood 30 may ensure that the distal face 34 of the hood 30 remains in fluid communication with the vacuum source 52 when vacuum is applied via the lumen 26. In addition or alternatively, the extension of the mid catheter distal tip 25 into the chamber 36 of the vacuum hood 30 may prevent the vacuum hood 30 from crossing the path of the needle tip 45 and being penetrated by the needle tip 45, e.g., when the vacuum hood 30 is pressed against or encounters anatomy, e.g., a wall of the heart.

In addition or alternatively, the vacuum hood 30 may include one or more radiopaque markers 39, which may be used independently or in conjunction with one or more radiopaque markers on the mid catheter 20, such as the distal tip 25. For example, as shown in FIG. 2, the vacuum hood 30 may include two annular radiopaque rings or markers 39*a*, 39*b* spaced apart axially from one another. The annular markers 39 may extend continuously around the circumference of the hood 30 or may extend discontinuously around the circumference, e.g., defining by a plurality of lines, dots, and the like that are spaced apart from one another but define a circumferential line. As shown, a first annular marker 39*a* may be located at or near the distal face 34 and a second annular marker 39*b* spaced a predetermined distance proximally from the first marker 39*a*, e.g., adjacent the outward fold 38*a*. The markers 39 may be created similar to the materials and methods described elsewhere herein, e.g., by doping and/or embedding or applying various radiodense materials to the hood material. In addition or alternatively, the entire hood 30 may be made at least partially radiopaque. In an exemplary embodiment, the vacuum hood 30 may be formed from silicone doped with approximately 20% barium sulfate and the markers 39 may be formed from of silicone doped with tungsten and applied to the hood 30, e.g., to distinguish the base material and markers 39 under fluoroscopic imaging.

Figures 3A, 3B:
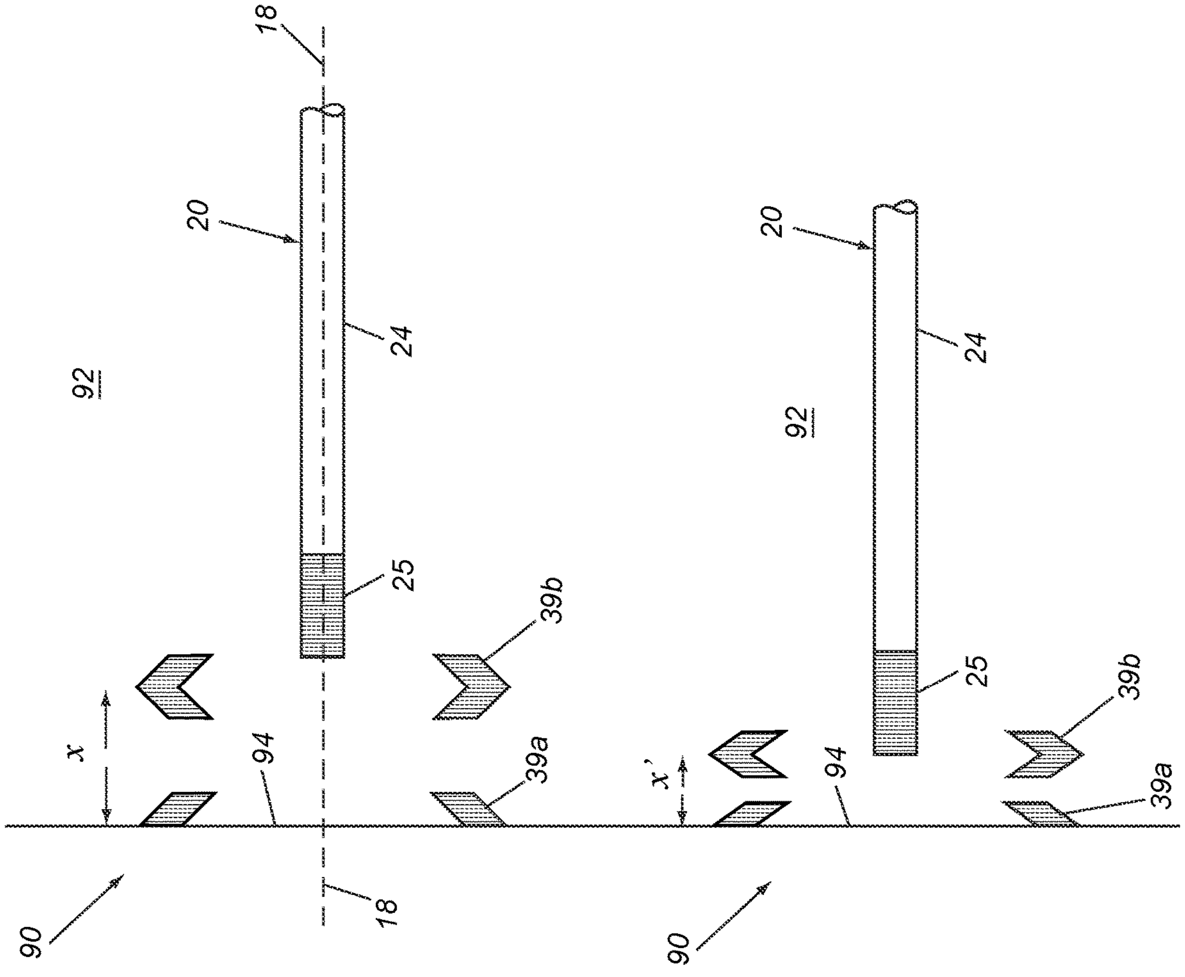
FIGS. 3A and 3B are fluoroscopic images showing appearance of the radiopaque features of the vacuum hood of FIG. 2 before and after attachment, respectively, of the vacuum hood to a tissue wall.
Figure 6A:
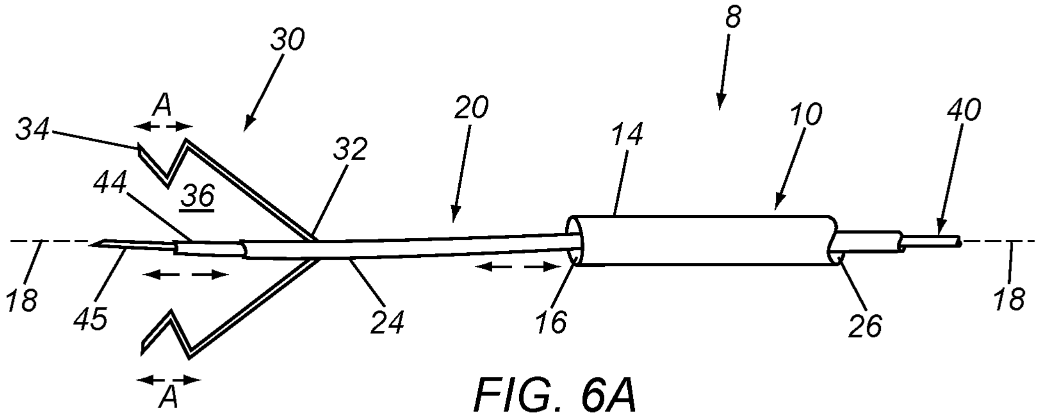
FIGS. 6A-6C show use of a vacuum hood to enable secure oblique entry of a needle into a tissue wall, e.g., using the system shown in FIGS. 1 and 5.

The markers 39 may facilitate positioning the vacuum hood 30 and/or confirm when the distal face 34 is seated and/or attached to a tissue structure, e.g., to a wall of a heart. For example, FIGS. 3A and 3B show exemplary fluoroscopic views of the vacuum hood 30 of FIG. 2, showing the relative position of the markers 39 before and after attachment of the distal face 34 to a wall 94 of a heart 90. FIG. 3A shows a representative image that may be obtained when the vacuum hood 30 is in the expanded configuration, e.g., when deployed freely within a chamber 92 of a heart 90, e.g., as shown in FIG. 6A. In this configuration, the markers 39*a*, 39*b* may be spaced apart from one another by a distance "X" corresponding to the distance between the markers 39*a*, 39*b* with the hood 30 in a relaxed configuration. During manipulation of the system 8 within the chamber 92, the distal face 34 of the vacuum hood 30 may initially come into contact with a tissue surface, e.g., the wall 94 of the heart 90, as shown in FIG. 3A. As the face 34 of the hood 30 is pressed against the wall 94 and a vacuum is applied within the chamber 36, the hood 30 may become attached and/or otherwise fixed to the wall 94 due to the vacuum, thereby compressing the hood 30 axially and directing the markers 39*a*, 39*b* closer together, e.g., to a smaller distance "X'", as shown in FIG. 3B. This new spacing may provide visual confirmation that the hood 30 is secured to the wall 94, whereupon an injection and/or other procedure may be performed, as described further elsewhere herein.

Figure 4A:
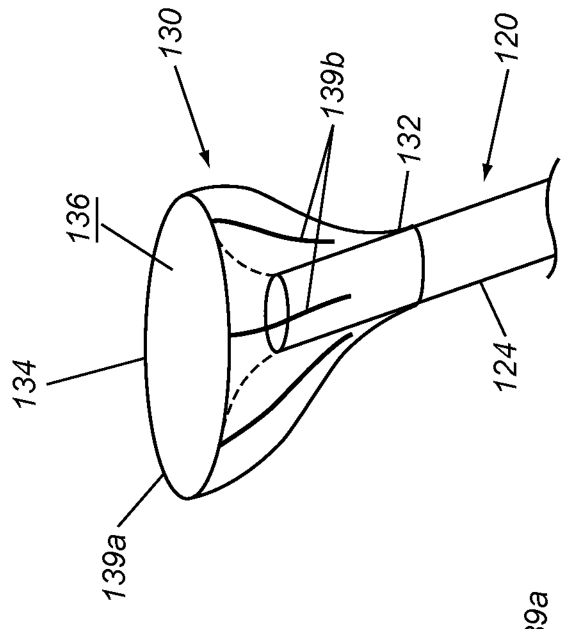
FIGS. 4A and 4B show side views of another embodiment of a vacuum hood including fluoroscopic features, showing the vacuum hood before and after attachment, respectively, to a tissue wall.
Figure 4B:
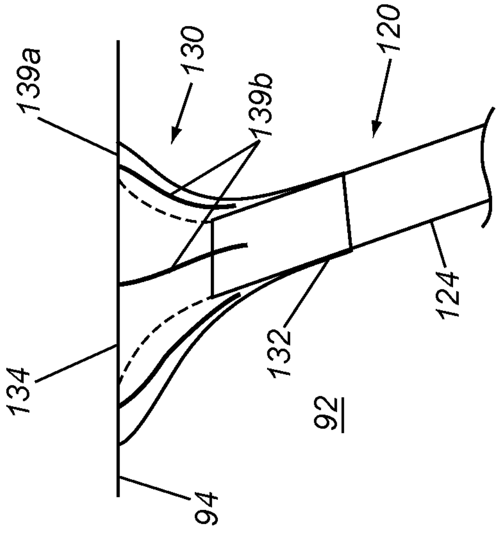

Alternatively, other configurations of markers may be provided on a vacuum hood to facilitate positioning and/or confirming when the hood is attached to a tissue structure. For example, FIGS. 4A and 4B shown another embodiment of a mid catheter 120 carrying a vacuum hood 130, which may be constructed generally similar to other embodiments herein. However, in this embodiment, the hood 130 includes a first annular marker, e.g., a radiopaque ring 139*a*, provided at the distal face and two or more radiopaque stripes or bands 139*b* that extend at least partially along the length of the hood 130, i.e., partially between the proximal end 132 and the distal face 134. FIG. 4A shows the hood 130 in a relaxed or expanded configuration, e.g., when the hood 130 is deployed from an outer catheter (not shown), and the markers 139*b* extend generally axially towards the distal face 132. FIG. 4B shows the hood 130 in a compressed configuration, e.g., when pressed against a wall 94 within a chamber 92 of a heart and when vacuum is applied to attach the hood 130 to the wall 94. As shown, the radiopaque ring 139*a* may provide visual confirmation when the distal face 134 is pressed against the wall 93. In addition, the hood 130 may collapse partially radially inwardly when the vacuum is applied, thereby causing the markers 139*b* to move closer together, i.e., reducing the circumferential distance between adjacent markers 139*b*, all of which may be observed using fluoroscopy or other imaging to confirm the hood 130 has been successfully sealed and attached to the wall 94.

Returning to FIG. 1, the injection catheter 40 also includes a proximal end 42, a distal end 44, and at least one lumen 46 extending between the proximal and distal ends 42, 44, e.g., from a port in a handle or hub 43 to an outlet 45*a* in a distal tip 45, e.g., as shown in FIG. 2. The injection catheter 40 may be sufficiently flexible along its length, e.g., to enable advancement through the primary lumen 26 of the mid catheter 20 along a tortuous path created by the primary lumen 26, e.g., through a patient's vasculature from a percutaneous entry site into a chamber of a heart (not shown), as described elsewhere herein. The distal end 44 of the injection catheter 40 may terminate in a needle tip 45, e.g., having a size between 22 and 28 gauge, or between 26 and 28 gauge, and having a beveled, multi-faceted grind, trocar grind, or other sharpened shape, as desired to facilitate penetration into tissue.

Figure 6B:
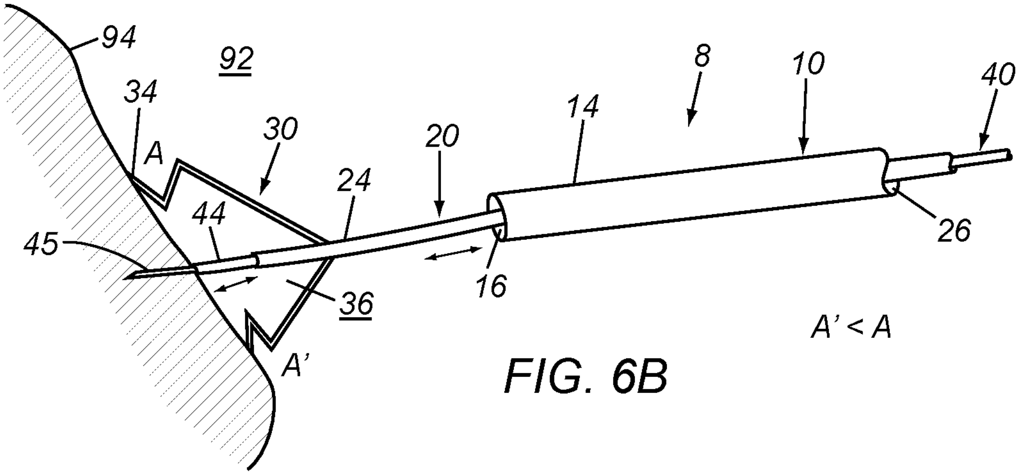
Figure 6C:
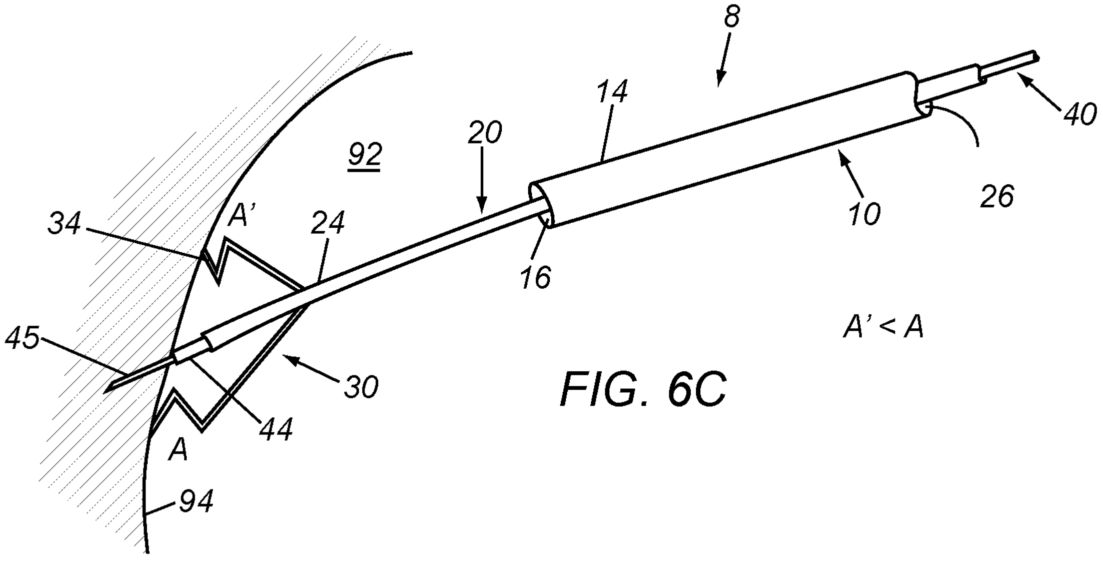

Optionally, the distal end 44 of the injection catheter 40 may include a step down, e.g., a blunt surface from which the needle tip 45 extends, e.g., similar to the needle device shown in FIGS. 6A-6C, which may reduce the risk of inserting the needle tip 45 too far into tissue. In addition, as shown in FIG. 1, the handle 43 may include a port having one or more connectors, e.g., a Luer connector, for connecting a syringe or other source of injectable material 54 to the handle 43 for delivery into the needle lumen 46 and out the outlet 45*a*. Exemplary embodiments of needle devices that may be used for the injection catheter are disclosed in U.S. Publication No. 2017/0119156, the entire disclosure of which is expressly incorporated by reference herein.

Generally, the system 8 of FIG. 1 may be used to navigate through a patient's body, e.g., through the patient's vasculature into a chamber of the patient's heart, to perform one or more injections using the injection catheter 40. For example, the system 8 may be used to access a left ventricle, e.g., using a retrograde aortic approach or an approach via the inter-atrial septum (not shown). Once in the heart, the vacuum hood 30 may be used to provide stability/attachment to the endocardial surface to facilitate introduction and maintenance of the needle tip 45 into the heart wall 94 to perform an injection. The vacuum hood 30 may be sized to accommodate typical topological features of the heart wall, for example, trabeculation in the ventricles, while maintaining a desired seal with the wall. In exemplary embodiments, the distal face 34 of the vacuum hood 30 may have a diameter in the expanded configuration between about four and fifteen millimeters (4-15 mm) or between about five and ten millimeters (5-10 mm). The combination of cross-section, material selection, mechanical design, and applied vacuum pressure may be adapted to provide sufficient attachment force in order to enable needle penetration, e.g., even without significant back support from the injection catheter 40.

Returning to FIG. 1, the injection catheter 40 also includes a proximal end 42, a distal end 44, and at least one lumen 46 extending between the proximal and distal ends 42, 44, e.g., from a port in a handle or hub 43 to an outlet 25*a* in a distal tip 25, e.g., as shown in FIG. 2. The injection catheter 40 may be sufficiently flexible along its length, e.g., to enable advancement through the primary lumen 26 of the mid catheter 20 along a tortuous path created by the primary lumen 26, e.g., through a patient's vasculature from a percutaneous entry site into a chamber of a heart (not shown), as described elsewhere herein. The distal end 44 of the injection catheter 40 may terminate in a needle tip 45, e.g., having a size between 22 and 28 gauge, or between 26 and 28 gauge, and having a beveled, multi-faceted grind, trocar grind, or other sharpened shape, as desired to facilitate penetration into tissue.

Figure 5:
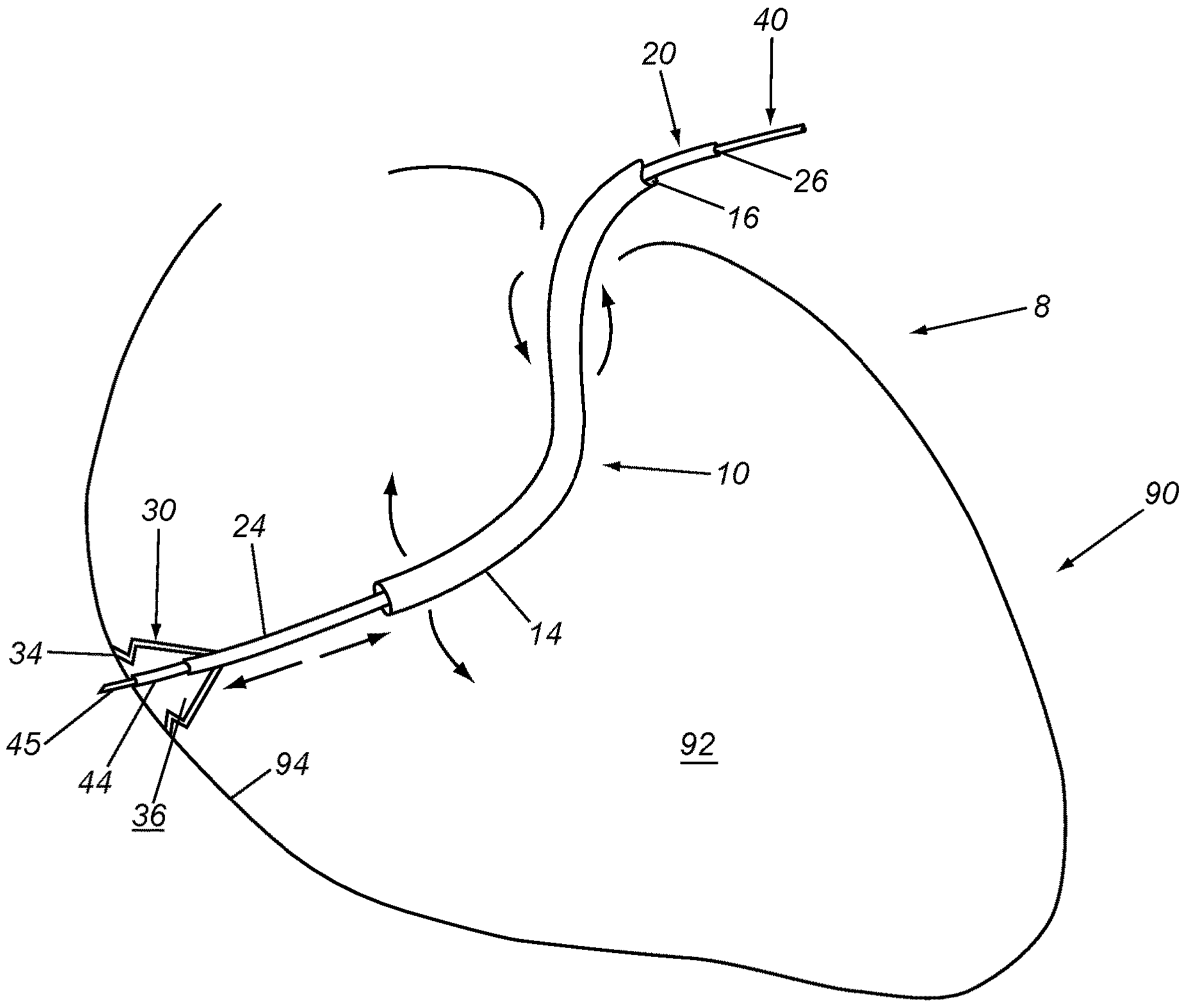
FIG. 5 is a cross-sectional view of a heart, showing a catheter system with outer catheter, mid catheter, vacuum hood and injection catheter being manipulated within a chamber of the heart.

Turning now to FIG. 5, basic navigation of the system 8 within a chamber 92 of a heart 90, e.g., a left ventricle, is shown. The distal end 14 of the outer catheter 10 may be navigated into the chamber 92, e.g., from a percutaneous entry site (not shown) through any intervening body lumens. As described previously, optionally, a distal segment of the outer catheter 10 may have a predetermined or variable curve, e.g., biased to a predetermined curvilinear shape and/or steerable or otherwise deflectable from the proximal end 12 (not shown in FIG. 5; see FIG. 1). The outer catheter 10 may be advanced, retracted, rotated, and/or deflected, as desired, e.g., to provide alignment of its distal end 14 with a target location in the heart 90.

Once alignment is achieved, the mid catheter 20 may be advanced to direct the distal end 24 and hood 30 out of the lumen 16, e.g., until contact is made between the hood 30 and the heart wall 94 at the target location. For example, if the mid catheter 20 is pre-loaded into the lumen 16 with the hood 30 disposed adjacent the distal end 14, the mid catheter 20 may be advanced sufficiently to deploy the hood 30, which may resiliently expand to the expanded condition, e.g., as shown in FIG. 6A. Alternatively, if the mid catheter 20 is initially outside the outer catheter 10, the hood 30 may be directed to the collapsed configuration and the hood 30 and mid catheter 20 may be loaded into the outer catheter 10, e.g., through the port 29*a* into the lumen 16 (not shown; see FIG. 1) and then deployed from the outer catheter distal end 14 within the chamber 92. Alternatively, the hood 30 may start and remain deployed, e.g., positioned immediately adjacent the distal end 14 of the outer catheter 10, e.g., to provide a substantially atraumatic bumper, which may facilitate advancement of the outer catheter 10, e.g., through an aortic valve or other tissue structure along the path of introduction (not shown).

Contact of the hood distal face 34 with the wall 94 may be identified fluoroscopically, e.g., using the markers 39, 25 on the hood 30 and/or mid catheter 20, as described elsewhere herein. With the hood 30 in close proximity to and/or in direct contact with the wall 94, vacuum may be applied to the primary lumen 26 of the mid catheter 20 (by activating the vacuum source 52 shown in FIG. 1) and thus transmitted to the chamber 36 of the hood 30, facilitating attachment of the hood 30 to the heart wall 94.

For example, as the face 34 of the hood 30 comes into contact with the wall 94, the hood 30 may be displaced, bent, or otherwise moved relative to the distal tip 25 of the catheter 20, which may facilitate identification of the surface of the wall 94 under fluoroscopy. Further, the relative position of the hood markers 39 to the mid catheter distal tip 25 may change as the tissue surface is encountered. For example, in FIG. 6A, the distal tip 25 and hood markers 39 are shown in generally straight alignment, e.g., aligned concentrically with a central axis 18 of the system 8. However, when a surface is encountered, the markers 25, 39 may become misaligned due to the flexible connection between the hood 30 and mid catheter 20, e.g., if the hood 30 is deflected laterally relative to the distal end 24 of the hood, e.g., as shown in FIGS. 6B and 6C.

Optionally, the hood 30 may include one or more features that allow the hood 30 to conform to a tissue surface that is not orthogonal to the longitudinal axis 18 of the system 8. For example, the hood 30 may include one or more features enabling the hood 30 to bend relative to the longitudinal axis 18. In an exemplary embodiment, the hood 30 may include a mid segment fold, bend, bellows, or other feature enabling the hood 30 to compress on one side as tissue is encountered obliquely, e.g., as shown in FIGS. 6B and 6C. Alternatively, the proximal narrowed portion of the hood 30 may simply be sufficiently flexible to allow the distal face 34 of the hood 30 to turn towards the tissue as a tissue wall 94 is encountered. As previously described, the distal tip 25 of the mid catheter 20 may extend at least partially into the chamber 34 of the hood 30 to ensure transmission of vacuum to the distal face 34, e.g., even in the case of partial collapse of a proximal region of the hood 30. Thus, the vacuum hood 30 may attach to the tissue wall 94 to enable stable entry and maintenance of the needle tip 45 into tissue despite encountering the wall 94 at an angle or obliquely.

In addition or alternatively, in another option, a distal segment of the mid catheter 20, e.g., the segment extending beyond the outer catheter distal end 14 and the mid catheter distal tip 25, e.g., as shown in FIG. 5, may be formed from substantially flexible material such that, during or after attachment, heart wall motion may be accommodated without causing detachment of the hood 30 from the wall 94. Thus, in addition to transmitting vacuum and providing extension to navigate, the distal flexible segment may act as a suspension system or shock absorber between the outer catheter 10 and the hood 30, thereby facilitating stable attachment. Once the hood 30 is substantially attached to the heart wall 94, the needle tip 45 may be advanced into the wall 94 to injection one or more agents into the underlying tissue, e.g., as shown in FIG. 6B.

It will be appreciated that when vacuum is applied to the chamber 36 of the hood 30 and when the distal face 34 of the hood 30 forms a seal with the wall 94, the decrease in pressure within the chamber 34 may lead to at least partial collapse of the hood 30, or more specifically, to at least partial axial foreshortening of the hood 34, e.g., as shown in FIGS. 6B and 6C. In conjunction with such foreshortening, the radiopaque markers 39*a*, 39*b* may move closer together, as represented in the fluoroscopic image of FIG. 3B, or otherwise exhibit a change in special relationship that is readily appreciated fluoroscopically, thus providing a visual indicator of attachment of the hood 30 to the wall 94.

Thus, the radiopaque features 39, 25 of the hood 30 and/or the mid catheter 20 may be used to identify the location of the heart wall 94 and/or secure attachment of the hood 30 to the heart wall 94. Further, a periodic change in the relative position of the markers 39, 25 may be identified, e.g., due to contraction of the heart wall 94. In similar fashion, if the needle tip 45 is made at least partially radiopaque, the needle tip 45 may be visualized relative to other fluoroscopic markers of the system 8, e.g., the markers 39 and/or 25. Thus, the user may be able to verify that the needle tip 45 is extending a predetermined distance beyond, for example, the distal radiopaque marker 39*a* of the hood 30. In the attached state, this distal marker 39*a* may substantially delineate the wall 94 of the heart 90, such that the depth of penetration of the needle tip 45 into the wall 94 may be estimated based on the distance beyond the distal marker 39*a*. The injection device 40 may then be used to deliver one or more therapeutic and/or diagnostic materials, e.g., cells, agents, filler materials, gels, and/or other substances into the myocardium beyond the wall 94.

It will be appreciated that the hood 30 may provide a substantially isolated working area for performing injections and/or other procedures. This may be of particular importance where material to be injected provides a degree of embolic risk. For example, if an injection is made with a needle tip not fully engaged in the target tissue and/or if injected material leaks back out of the injection site and/or if injected material otherwise becomes free in the chamber 34, the hood 30 may isolate the free injected material and the vacuum source 52 may cause the free material to be aspirated through the lumen 26 of the mid catheter 20, rather than released into the chamber 92 of the heart 90.

Figure 7:
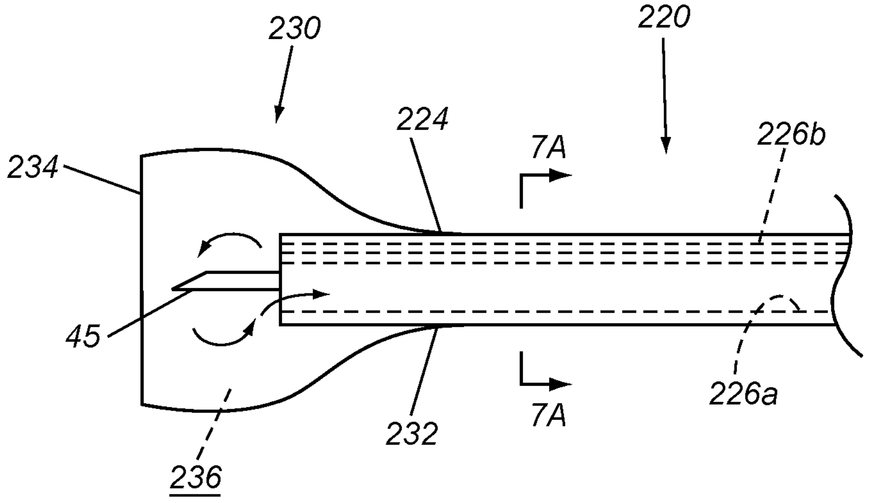
FIG. 7 is a side view of another exemplary embodiment of a mid catheter including a vacuum hood and a peripheral lumen for infusion/circulation of fluid within an interior chamber of the vacuum hood.
Figure 7A:
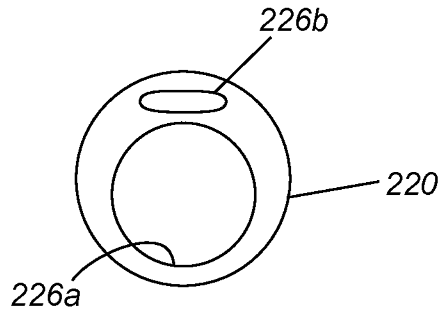
FIG. 7A is a cross-sectional view of the mid catheter of FIG. 7, taken along plane 7A-7A.

Turning to FIG. 7, another embodiment of mid catheter 220 is shown that includes a vacuum hood 230 carried on a distal end 224 of the mid catheter 220. Similar to the previous embodiments, the mid catheter 220 includes a primary lumen 226*a* communicating with a chamber 234 of the hood 230, e.g., to apply a vacuum within the chamber 234 and distal face 234 to attach the hood 230 to a tissue structure (not shown). In addition, the mid catheter 220 includes a secondary or peripheral lumen 226*b*, e.g., offset from primary lumen as shown in FIG. 7A, adapted for infusion of fluid. As vacuum is applied to the mid catheter primary lumen 226*a*, blood may be drawn into the primary lumen 226*a*, e.g., before attachment of the distal face 234 to a tissue structure, in the case of partial attachment, and/or at the point of detachment from tissue. Blood drawn into the primary lumen 226*a*, if left static, may potentially clot and provide a possible source of embolic debris, e.g., as the injection device 40 is translated within the primary lumen 226*a*, or in the event that the lumen 226*a* is flushed. In addition or alternatively, a source of vacuum may be coupled to the secondary lumen 226*b*, e.g., to provide the vacuum to the chamber 234 and/or to augment the vacuum applied via the primary lumen 226*a*.

To avoid this situation, the peripheral lumen 226*b* may be used to infuse fluid, e.g., heparin, heparinized saline, and/or other anticoagulant or dilutive media into the chamber 236. The fluid may be drawn back into the primary lumen 226*a* of the mid catheter 220 under vacuum and thereby diluting, clearing, and/or reducing the clotting potential of blood introduced into that lumen.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A catheter for performing a procedure within a patient's body, comprising:

a tubular member comprising a proximal end, a distal end sized for introduction into the patient's body, and a lumen extending between the proximal and distal ends;

a vacuum hood including a proximal end attached to the tubular member distal end and a distal face disposed distally beyond the tubular member distal end, the vacuum defining a chamber communicating with the tubular member lumen;

one or more annular features between the vacuum hood proximal end and the distal face to accommodate one or both of axial foreshortening and elongation of the vacuum hood;

an annular first radiopaque marker extending circumferentially around the vacuum hood at the distal face; and an annular second radiopaque marker extending circumferentially around the vacuum hood spaced from the first radiopaque marker configured to provide a spatial relationship that visibly changes under fluoroscopy when the vacuum hood is under sealed vacuum, wherein the tubular member further comprises a blunt distal tip permanently attached to the tubular member distal end and wherein the vacuum hood proximal end is permanently attached to the tubular member distal end proximal to the distal tip such that the distal tip extends a predetermined distance into the chamber, the distal tip defining an outlet through which a device that is inserted through the lumen extends during the procedure.

2. The catheter of claim 1, wherein the second radiopaque marker extends circumferentially around the vacuum hood at a location proximal to the distal face, such that a distance between the first and second radiopaque markers provides the spatial relationship that visibly changes under fluoroscopy when the vacuum hood is under sealed vacuum.

3. The catheter of claim 2, wherein the second radiopaque marker is located at a first annular feature of the one or more annular features such that the distance between the first and second radiopaque markers foreshortens when the first annular feature foreshortens when the vacuum hood is under sealed vacuum.

4. The catheter of claim 2, wherein the one or more features comprise one or more annular folds defining a bellows offset a predetermined distance proximal to the distal face to accommodate one or both of axial foreshortening and elongation of the vacuum hood.

5. The catheter of claim 2, wherein the one or more features comprise an annular region offset a predetermined distance proximal to the distal face, the annular region comprising material that is more flexible than material immediately proximal and immediately distal to the annular region to provide a bendable region of the vacuum hood.

6. The catheter of claim 2, wherein the material of the flexible region is doped to provide the second radiopaque marker.

7. The catheter of claim 2, wherein the second radiopaque marker is applied at the flexible region or proximal to the flexible region.

8. The catheter of claim 1, further comprising a plurality of markers that extend at least partially axially between the vacuum hood proximal end and the distal face such that a circumferential distance between adjacent markers of the plurality of markers further provides the spatial relationship that visibly changes under fluoroscopy when the vacuum hood is under sealed vacuum.

9. The catheter of claim 1, wherein the distal tip comprising radiopaque material to facilitate identification of the location of the distal tip relative to the radiopaque markers on the vacuum hood.

10. The catheter of claim 9, wherein the entire distal tip is radiopaque.

11. A catheter for performing a procedure within a patient's body, comprising:

a tubular member comprising a proximal end, a distal end sized for introduction into the patient's body terminating in a blunt distal tip, and a lumen extending between the tubular member proximal and distal ends;

a vacuum hood attached to the distal end of the tubular member proximal to the distal tip such that the distal tip extends a predetermined distance into the hood;

at least two radiopaque markers extending circumferentially around the hood and spaced apart from one another such that a distance between the at least two radiopaque markers provides a spatial relationship that visibly changes under fluoroscopy to confirm when the vacuum hood is under sealed vacuum; and a radiopaque tip marker permanently attached to the tubular member distal end to define the distal tip and extending into the hood configured to identify an orientation of the hood based on the spatial relationship of the at least two radiopaque markers relative to the tip marker, wherein the distal tip comprises an outlet through which a device that is inserted through the lumen extends during the procedure, and wherein a proximal end of the vacuum hood is permanently attached to the tubular member distal end proximal to the distal tip such that the tip marker extends a predetermined distance into a chamber of the vacuum hood.

12. The catheter of claim 11, wherein the at least two radiopaque markers comprise:

an annular first radiopaque marker extending circumferentially around the vacuum hood at a distal face of the distal end; and an annular second radiopaque marker extending circumferentially around the vacuum hood at a location proximal to the distal face.

13. A system for performing a procedure within a patient's body, comprising:

a tubular member comprising a proximal end, a distal end sized for introduction into the patient's body, and a lumen extending between the proximal and distal ends;

a vacuum hood attached to the distal end;

a radiopaque distal tip permanently attached to the distal end and extending at least partially into the vacuum hood, the distal tip defining an outlet; and at least two radiopaque markers extending circumferentially around the vacuum hood and spaced apart from one another such that a distance between the at least two radiopaque markers provides a spatial relationship that visibly changes under fluoroscopy to confirm when the vacuum hood is under sealed vacuum.

14. The system of claim 13, wherein the vacuum hood comprises a proximal end attached to the distal end proximal to the distal tip and a distal face shaped for contacting a tissue surface within the patient's body.

15. The system of claim 14, wherein the vacuum hood includes one or more annular features between the vacuum hood proximal end and the distal face to accommodate one or both of axial foreshortening and elongation of the vacuum hood.

16. The system of claim 15, wherein one of the one or more annular features are doped with radiopaque material to define a first marker of the at least two radiopaque markers on the vacuum hood.

17. The system of claim 16, wherein a second marker of the at least two radiopaque markers extends circumferentially around the vacuum hood at the distal face, such that a distance between the first and second markers provides the spatial relationship that visibly changes under fluoroscopy when the vacuum hood is under sealed vacuum.

18. The system of claim 14, wherein the vacuum hood includes one or more annular folds defining a bellows offset a predetermined distance proximal to the distal face to accommodate axial foreshortening and elongation of the vacuum hood.

19. The system of claim 14, wherein the vacuum hood includes an annular region offset a predetermined distance proximal to the distal face, the annular region comprising material that is more flexible than material immediately proximal and immediately distal to the annular region to provide a bendable region of the vacuum hood.

20. The system of claim 14, wherein the at least two radiopaque markers comprise a first annular marker that extends circumferentially around the vacuum hood at the distal face and an annular second radiopaque marker extending circumferentially around the vacuum hood at a location proximal to the distal face.

21. The system of claim 18, wherein a first marker of the at least two radiopaque markers extends circumferentially around the hood adjacent an annular fold of the one or more annular folds.

22. The system of claim 14, further comprising an injection device sized for introduction through the lumen and out the outlet in the distal tip.

23. The system of claim 14, wherein the distal tip extends partially into the hood such that the distal tip is spaced proximally from the distal face, the system further comprising a source of vacuum in communication with the lumen to generate vacuum within the chamber, and consequently at the distal face.

* * * * *